United States Patent [19]

Berenbaum et al.

[11] Patent Number: 4,990,623

[45] Date of Patent: Feb. 5, 1991

[54] SULFONATED 2-(2'-HYDROXYARYL)-2H-BENZO-TRIAZOLES AND/OR SULFONATED AROMATIC FORMALDEHYDE CONDENSATES

[76] Inventors: Morris B. Berenbaum, 59 Crest Dr., Summit, N.J. 07901; John H. Bonfield, 183 Lyons Dr., Basking Ridge, N.J. 07920; Charles J. Cole, 11560 Teterling Rd.; Paul W. Harris, 11410 Chalkley Rd., both of Chester, Va. 23831; Thomas P. J. Izod, 112 Victoria Dr., Basking Ridge, N.J. 07920; Harry E. Ulmer, Rte. 2, Box 3, Cameron, S.C. 29030; Frederick R. Hopf, 350 Parsippany Rd., Parsippany, N.J. 07054; James T. Yardley, 40 Macculloch Ave., Morristown, N.J. 07960; Karen M. Bland, 144 Heritage La., Hamburg, N.J. 07419

[21] Appl. No.: 384,234

[22] Filed: Jul. 24, 1989

Related U.S. Application Data

[63] Continuation-in-part of Ser. No. 111,873, Oct. 21, 1987, abandoned, which is a continuation-in-part of Ser. No. 889,705, Jul. 28, 1986, abandoned, and a continuation-in-part of Ser. No. 74,487, Jul. 23, 1987, abandoned, which is a continuation-in-part of Ser. No. 904,433, Sep. 8, 1986, abandoned.

[51] Int. Cl.$^5$ ............................................. C07D 249/20
[52] U.S. Cl. ........................................ 548/260; 8/115; 8/194; 8/573; 548/101
[58] Field of Search ................................ 548/260, 101

[56] References Cited

U.S. PATENT DOCUMENTS

| | | | |
|---|---|---|---|
| 3,897,421 | 7/1975 | Aebli | 548/217 |
| 4,001,266 | 1/1977 | Rody et al. | 548/260 |
| 4,226,763 | 10/1980 | Dexter et al. | 548/257 |
| 4,278,589 | 7/1981 | Dexter et al. | 548/260 |
| 4,668,235 | 5/1987 | Evans et al. | 548/260 |
| 4,786,728 | 11/1988 | Schwaiger et al. | 548/260 |
| 4,816,574 | 3/1989 | Schwaiger et al. | 548/260 |

FOREIGN PATENT DOCUMENTS

| | | | |
|---|---|---|---|
| 1154778 | 10/1983 | Canada | 548/260 |
| 0117672 | 7/1982 | Japan | 8/442 |

Primary Examiner—Donald G. Daus

[57] ABSTRACT

A new class of sulfonated 2-(2'-hydroxyaryl)-2H-benzotriazole compounds and method for using them and other sulfonated hydroxyaryl benzotriazoles on nylon fibers to improve stain resistance and dye lightfastness has been discovered. A process is provided for improving stain resistance of nylon fibers by treatment with sulfonated aromatic-formaldehyde condensate and fluorinated dry soil resist agents.

5 Claims, No Drawings

SULFONATED 2-(2'-HYDROXYARYL)-2H-BENZOTRIAZOLES AND/OR SULFONATED AROMATIC FORMALDEHYDE CONDENSATES

This is a continuation-in-part of U.S. Ser. No. 111,873 filed Oct. 21, 1987 now abandoned, which is a continuation-in-part of U.S. Ser. No. 889,705 filed July 28, 1986, now abandoned, and of U.S. Ser. No. 74,487 filed July 23, 1987, now abandoned, which in turn is a continuation-in-part of U.S. Ser. No. 904,433 filed Sept. 8, 1986, now abandoned.

BACKGROUND OF THE INVENTION

This invention relates to sulfonated and sulfated hydroxy benzotriazoles and their use to improve stain resistance and dye lightfastness in nylon fibers. Particularly useful are new sulfonated and sulfated 2-(2'-hydroxyaryl)-2H-benzotriazoles.

This invention also relates to stain resistant polyamide fibers treated with sulfonated aromatic-formaldehyde condensation products and fluorinated dry soil release agents.

DESCRIPTION OF THE PRIOR ART

The prior art is replete with compositions and processes for improving the stain resistance of polyamide (nylon) fibers. The advantages of stain resistance is apparent for many of the uses of nylon, especially when used in carpets. U.S. Pat. Nos. 3,663,157 and 3,519,669 disclose certain formaldehyde condensation products useful as stain resists. The use of fluorine containing agents to impart soil resistance of nylons is well known as illustrated by U.S. Pat. Nos. 4,414,277; 4,209,610; 4,195,105 and 4,192,754, all hereby incorporated by reference. U.S. Pat. No. 3,844,712 to Frickenhaus discloses a method of improving the wet fastness of polyamides dyed with cationic dyes by treatment with the salts of condensation products of formaldehyde and sulfonated diphenyl ethers. However, Frickenhaus does not disclose or recognize any improvement in stain resistance and especially, Frickenhaus does not recognize that his condensation products would increase the stain resistance of a polyamide fiber treated with a dry soil release agent.

The unsulfonated or unsulfated precursor 2-(2'-hydroxyaryl)-2H-benzotriazoles (hereinafter sometimes called hydroxy benzotriazole or aryl benzotriazole) are disclosed for use to protect organic substances from light-induced deterioration in U.S. Pat. Nos. 4,226,763 and 4,278,589 both hereby incorporated by reference. Use of sulfonated 2-(2'-hydroxyaryl)-2H-benzotriazoles as photostabilizing agents for natural and synthetic fibers is disclosed in a published international application under the Patent Cooperation Treaty (PCT), Publication No. WO 84/02365 and in U.S. Pat. No. 4,668,235 hereby incorporated by reference.

SUMMARY OF THE INVENTION

In accordance with this invention there is provided a process for improving the stain resistance of polyamide fibers which comprises treating the fibers with a sulfonated aromatic-formaldehyde condensation product and a fluorinated dry soil release agent. Additionally, a process is provided for improving the stain resistance of such fibers by treatment with certain sulfonated aromatic-formaldehyde condensation products alone, i.e., sulfonated diphenyl ethers. Fibers treated in accordance with this invention exhibit excellent resistance to common anionic stain agents such as the food dye FD&C Red Number 40, as found in Cherry Kool-Aid TM.

Surprisingly, it has also been found that certain water soluble sulfonated or sulfated aryl benzotriazoles also improve resistance of synthetic nylon fibers to staining by common anionic stain agents, such as foods containing Acid Red 40 (Kool-Aid ®) dye, and these sulfonated or sulfated aryl benzotriazoles improve lightfastness of dye on the nylon fiber. Some of these sulfonated or sulfated aryl benzotriazoles are new compounds, namely, compounds having the structure

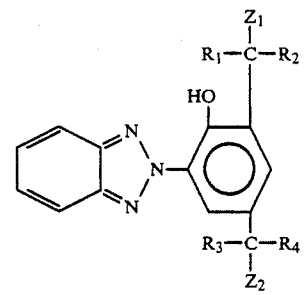

wherein $R_1$, $R_2$, $R_3$ and $R_4$ are independently the same or different alkyl groups and $Z_1$ and $Z_2$ are alkyl or sulfonated aryl group, provided at least $Z_1$ or $Z_2$ is sulfonated aryl group. The sulfonated aryl used should be such that the resulting compound is water soluble.

Mixtures of the compounds of the structure given above can be used to treat fibers to improve resistance to staining by anionic staining compounds such as Acid Red food dyes used in Kool Aid and also to improve lightfastness of dyes on nylon fibers. The fibers can be treated with the sulfonated hydroxy benzotriazoles of the structures given above, preferably in aftertreatment wherein the treatment is at a preferred pH of between about 2 and 5.

The method for improving resistance to staining by anionic staining compounds and to improve lightfastness of dyes on nylon fibers, also comprises treating the fibers with an aqueous solution of sulfonated hydroxy benzotriazole at mild temperatures selected from the group consisting of

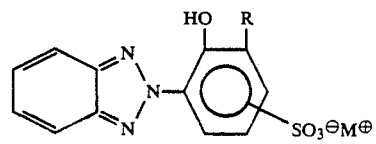

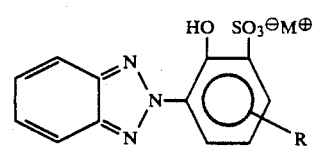

where R=secondary alkyl, tertiary alkyl or tertiary aralkyl, and M is a positive ion, such as alkali metal or hydrogen, particularly useful would be ammonium, aluminum, magnesium, lithium, sodium, potassium, zinc and other ions which do not result in a highly colored compound,

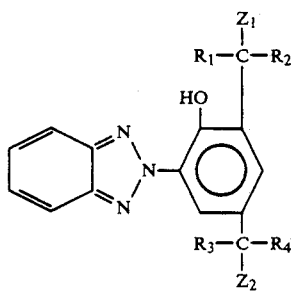

III where $R_1$, $R_2$, $R_3$, $R_4$, $Z_1$ and $Z_2$ are as defined above and

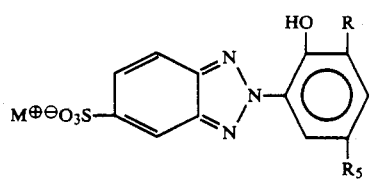

IV

We have discovered that compounds of the general structure

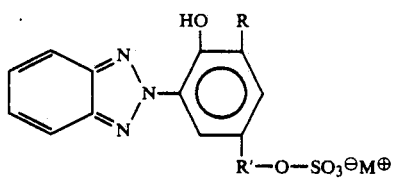

V where R is a secondary alkyl, tertiary alkyl group, and M = hydrogen or metal, especially

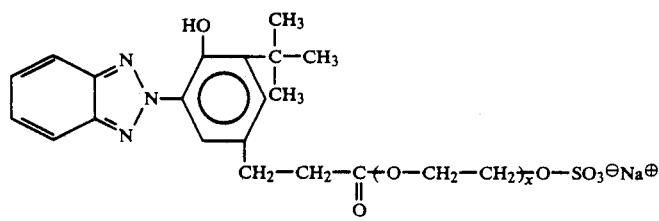

wherein the ionic sulfate group is located at the terminus of a heteroaliphatic chain of 6 to 30 atoms (preferably about 15 to 24 atoms) afford a surprising increase of photostability to polyamines relative to compounds VI and VII. The preferred heteroaliphatic is a polyether chain, such as the oligomer or polymer of a polyolefin oxide such as polyethylene oxide, polypropylene oxide, polybutylene oxide, and the like.

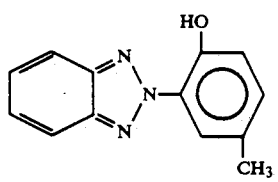

VI

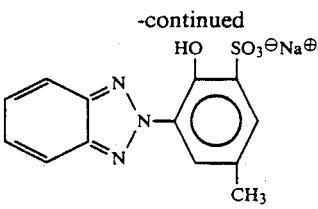

VII where M is a positive ion, such as alkali metal or hydrogen, R is tertiary alkyl or tertiary aralkyl and $R_5$ is a short chain alkyl.

The preferred method of treatment is an after-treatment at a pH of between about 2 and 5. The preferred treatment temperature is between about 30° C. and 90° C. The preferred time to aftertreat the fiber is after dyeing, preferably from about 10 to 30 minutes after dyeing. The compounds I, III and IV are also useful to improve properties of nylon materials in other forms, such as film.

DETAILED DESCRIPTION OF THE INVENTION

When not otherwise defined, as used in this specification alkyl means a paraffin hydrocarbon radical derived from an alkane by dropping at least one hydrogen atom, such radicals containing from one to about thirty carbon atoms.

As used in this specification, aryl means an aromatic radical derived from those characteristic six-carbon ring or the condensed six-carbon ring compounds such as benzene, naphthalene, phenanthrene, anthracene, etc. derived by dropping at least one hydrogen atom therefrom, e.g. phenyl, naphthyl, phenanthryl, anthryl and the like moieties.

The terms nylon and polyamide as used herein denote those synthetic long chain polyamides having recurring amide groups as an intregal part of the polymer chain. Exemplary of such polyamides are nylon 6, nylon 66, nylon 12, etc.

The aromatic compounds that may be condensed with formaldehyde for use in the process of this invention are those which contain up to 30 or more carbon atoms and preferably have at least one phenol or naphthyl group. The aromatic groups may be unsubstituted or substituted with hydroxyl, alkyl groups of 1 to 18 carbon atoms and/or fluoroalkyl of 1 to 10 carbon atoms, including prefluoroalkyl groups. The aromatic compounds may be composed of two or more aromatic rings bridged by —O—, —$SO_2$, —$C_nN_{2n}$—, —CO—, or a carbon to carbon bond. It will be understood that a necessary feature of the aromatic compound is its ability to condense with formaldehyde and to that extent a formaldehyde-reactive substitutent is necessary. Illustrative of the types of aromatic compounds that may be condensed with formaldehyde and used in the process of this invention are, benzenes, naphthalenes, xylenes,

ST-1130 bis-phenols, phenols, naphthols, diphenyl ethers, diphenyl sulfones, diphenyl ketones, diphenyl alkanes, dinaphthyl ethers, dina-ohthyl sulfones, dinaphthyl ketones, dinaphthyl sulfones, and the like. As indicated above, the aromatic compounds may be unsubstituted or substituted with hydroxyl, alkyl and/or perfluoroalkyl groups.

Preferably, the aromatic compound is first sulfonated and thereafter condensed with formaldehyde although the unsulfonated compounds may be first condensed with formaldehyde and the condensate then sulfonated. Sulfonation is preferably accomplished by direct addition of chlorosulfonic acid. Alternatively, $SO_3$ or sulfuric acid may be used although higher temperatures are required with the acid. Prior to reaction with formaldehyde, the sulfonated aromatic compound is diluted with water. An aqueous solution of formaldehyde is added with the mole ratio of sulfonated aromatic compound formaldehyde being in the range of 1.0 to 2.0, preferably 1.5 to 1.7.

More preferably, the sulfonated aromatic-formaldehyde condensation products are compounds having the following structure (hereinafter called the "preferred DPE condensate"):

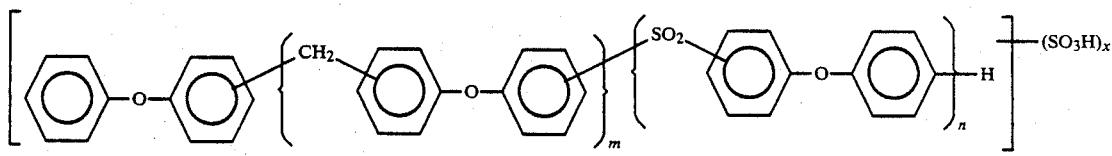

wherein m is 0 to 4, n is 0 to 3 and x is 1 to 5. Most preferred are the compounds wherein m is 0 or 1, n is 0 to 2 and x is 1 to 3, except the nonpreferred species are compounds wherein $m+n=0$ or 1 along with $x > \mu + m + 1$, or wherein $m=0$, $n=1$ and $x=2$. A particularly well-performing compound is when $m=1$, $n=0$ and $x=2$.

Although the use of fluorinated dry soil release (DSR) agents have been previously employed to impart stain resistance to polyamide carpet fibers, it has been found, in accordance with this invention, that the use of such DSR agent in conjunction with the sulfonated aromatic condensate results in a synergistic effect producing a superior stain resistance than either treatment agent alone. Additionally, the resistance of such fibers to ozone fading is surprisingly improved. The term fluorinated dry soil release agent as used herein is intended to denote those agents known and used in the art to impart increased soil resistance to polyamide fibers, particularly, carpet fibers. Particularly useful in the process of this invention are the fluorinated dry soil release agents of the types disclosed in U.S. Pat. Nos. 4,191,754; 4,604,316 and 4,605,587, which are incorporated herein by reference It is preferred that the fiber first be treated with the fluorinated dry soil release agent and thereafter with the sulfonated aromatic-formaldehyde condensate although that sequence may be reversed.

The compounds used in the process of this invention impart excellent stain resistant properties when applied to polyamide surfaces. While not wanting to be bound by any theory, it is believed that under the special application conditions, the sulfonated aromatic-formaldehyde condensate products saturate the nylon near the surface of the fiber. This results in a high negative charge density which forms an ionic barrier and thereby inhibits the sorption of water soluble food dyes such as are found in artificially colored foods.

The sulfonated aromatic-formaldehyde condensates useful in accordance with this invention are water soluble and can be applied to nylon in a variety of ways. Typically, the compounds are applied to dyed fiber from either a dilute or concentrated aqueous solution with a concentration range between 0.001 and 75 weight percent. The solution is contacted with the polyamide fiber for 5 seconds to 45 minutes at temperatures ranging from room temperature to about 100° C. The pH of this solution should be between 1.0 and 5.0, preferably about 2.0. It has been found that when the pH of the solution is at the lower pH values the percent exhaust and stain resist property of the treated fiber is significantly improved. For this reason, it is preferred to employ sulfonated aromatic condensates with $-SO_3H$ groups instead of sulfonate salts. After treatment the fiber is water extracted and oven dried at 120° C. The sulfonated condensates useful in this invention can be applied to dry or wet fiber either as a concentrated or dilute solution. The treated fibers should contain the sulfonated condensate in amounts of between 0.05 and 10% OWF (on the weight of fibers) and the treatment bath conditions should be maintained accordingly.

The method for applying the fluorinated dry soil release agent (DSR) to polyamide fibers is known in the art and is thus not necessary to describe in detail. In general, the fibers may be contacted with a spin finish containing the DSR agent in a known manner or other suitable procedures may be employed. The amount of DSR on the fibers resulting from the process of this invention should be between 0.05 and 1.0% on weight of fabric (OWF).

The treated nylon carpet fibers are tested for stain resistance in the following manner. A treated sample of nylon carpet yarn in circular knit sleeve form is placed on a non-absorbent surface and a small (10 ml) beaker containing 2 ml of staining solution, e.g., Cherry Kool-Aid ™ is inverted on the fabric and slowly agitated in such a manner that the liquid is retained within the beaker and in contact with the fabric until the termination of the test, or absorption of the staining solution by the fabric takes place. After 5 minutes, or other suitable period of time, the beaker and remaining solution are removed and any excess liquid on the fabric is blotted away with absorbent paper towels. The depth of the stained area is then visually assessed by use of the AATCC Gray Scale for staining, the AATCC Chromatic Transference Scale, or other suitable comparative method.

It has also been found, in accordance with this invention that certain sulfonated aromatic-formaldehyde condensates, namely those produced by reacting formaldehyde with sulfonated diphenyl ethers (DPE), can by themselves impart stain resistance to polyamide fibers. The DPE may be unsubstituted or substituted with 1-18 carbon alkyl or 1-10 carbon fluoroalkyl. These diphenyl ether condensation products are produced, as described above, by sulfonating DPE or its alkyl or fluoroalkyl derivitives and thereafter condensing with formaldehyde. Unsubstituted DPE is prefered but, prior to sulfonation the DPE may be alkylated or fluoralkylated. However, the alkylation process, generally conducted by a Friedel-Crafts type reaction, adds cost. Preferably the sulfonate is —$SO_3H$ as this results in a lower pH of the treatment solution. In addition, the treatment of polyamide fibers with the DPE condensate in conjunction with the above described DSR results in either fiber characteristics surpassing those obtained by either agent alone.

EXAMPLE 1

A diphenyl ether-formaldehyde condensation product is produced as follows to a reactor containing 170 grams of DPE is added 128 grams of chlorosulfonic acid over a 1 hour period at 50°-60° C. After air sweeping to remove HCl there is added 65 grams of water and thereafter, while maintaining the temperature at 50°-60° C. there is added 49 grams of a 37% (by weight) aqueous formaldehyde solution over a 30-minute period. The liquid is then digested for 10 hours at 100°-105° C. The product 265 grams in 107 grams of water is drained from the reactor. A mixture of the "preferred DPE condensate" compounds previously described was formed. A 7.5 gram dry nylon 6 sleeve is contacted with 0.15 grams of the condensation product so produced and 175 ml of water for 30 minutes at 71° C. The nylon 6 sleeve had been previously treated with a fluorinated dry soil release compound as described in Example 1 of U.S. Pat. No. 4,192,754 and mock dyed. The nylon sleeve is then squeezed and paper towel dried before placing in an oven at 120° C. for 30 minutes. A 5-minute stain test with a Cherry Kool-Aid TM solution gave a 5 rating on the Chromatic Transference Scale (5=best, 1=worst) compared to an untreated sleeve control rating of 1.

EXAMPLE 2

A 7.5 gram nylon 6 sleeve which had not been pretreated with a fluorinated dry soil release agent but which had been mock dyed was contacted with 0.15 grams of the condensation product produced in accordance with Example 1 in 175 ml of water for 30 minutes at 71° C. The nylon sleeve is then squeezed and paper towel dried before placing in an oven at 120° C. for 30 minutes. A 5-minute stain test with Cherry Kool-Aid TM solution gave a 3+ rating compared to a 1+ rating for the untreated sleeve control.

EXAMPLE 3

A diphenyl ether-formaldehyde condensation product is produced as follows: to a reactor containing 170 grams DPE in 500 ml of carbon disulfide there is added 30 grams $AlCL_3$. 334 grams of hexafluoroacetone is introduced over a three-hour period while the temperature is held at 0°-10° C. After dilution with ice water, phase separation and removal of $CS_2$, the product, a fluid liquid at 25° C., is treated with 128 grams of chlorosulfonic acid added over a one-hour period of 30°-50° C. There is then added 80 grams $H_2O$. Aliquots are taken from the reactor and a 37 weight percent formaldehyde aqueous solution is added such that the mole ratio of sulfonated DPE to formaldehyde ranges from 1.3 to 1.8. A 7.5 gram nylon 6 sleeve which had been previously treated with a fluorinated dry soil release agent as described in Example 1 of U.S. Pat. No. 4,192,754 is contacted with 0.15 grams of the condensation product so produced in 175 of water for 30 minutes at 71° C. The nylon 6 sleeve had been previously mock dyed. A 5-minute stain test with Cherry Kool-Aid TM solution gave a 5 rating.

EXAMPLE 4

A nylon 6 sleeve which had not been pretreated with a fluorinated dry soil release agent but which had been mock dyed was contacted with 0.15 grams of the condensation product produced in accordance with Example 3 in 175 ml of water for thirty minutes at 71° C. The nylon sleeve is squeezed and paper towel dried before placing in an oven at 120° C. for 30 minutes. A five-minute stain test with Cherry Kool-Aid TM solution gave a 4 rating.

EXAMPLE 5

A dihydroxy diphenyl sulfone formaldehyde condensate is sold under the trade name MESITOL PS by Mobay Chemical Company. Four nylon 6 sleeves composed of fibers previously treated with the DSR described in Example 1 of U.S. Pat. No. 4,192,754, and four nylon 6 sleeves containing no DSR, are contacted with a solution of the sulfonated aromatic condensate under conditions adjusted to result in treated sleeves containing 0.2%, 0.5%, 1.0% and 2.0%, OWF of the condensate. Stain testing of the resulting samples, along with two control samples, as described in Example 1, gave the following results:

| % OWF | No DSR | DSR Treated |
| --- | --- | --- |
| 0 | 1 | 2 |
| 0.2 | 1 | 3 |
| 0.5 | 2 | 4 |
| 1.0 | 2.5 | 5 |
| 2.0 | 3.5 | 5 |

An additional feature of the present invention lies in a process for treating polyamide fibers with the sulfonated aromatic-formaldehyde condensates described above in conjunction with treatment of the fibers with 0.1 to 5.0% (OWF) of the 2-(2-hydroxyaryl)-2H-benzotriazoles described in Examples 8 to 15. Surprisingly, the treatment with these benzotriazoles does not adversely affect the stain resistance characteristics obtained with the sulfonated aromatic-formaldehyde condensate while the lightfastness of the treated fibers exhibits significant improvement.

EXAMPLE 6

Nylon 6 sleeves predyed silver-gray as in Example 13 were treated with aqueous baths containing a condensate of formaldehyde and unsubstituted diphenyl ether prepared as described in Example 1 above, and the compounds described in Example 8 (Example 6a) and Example 9 (Example 6b). The bath temperature was 110° F. (38° C.) and pH 2.1. Similarly a control was prepared from a bath containing only the sulfonated DPE-formaldehyde condensate of Example 1 (Example 6c). Bath conditions and treatment time were such that the treated nylon contained 2.0% OWF of the DPE-formaldehyde concentrate and 0.5% OWF of the benzotriazole. After treatment stains were created on the sleeves with Cherry Kool-Aid TM containing FD & C Red 40 by forcing about 5 cc of the Kool-Aid TM into the fabric of the sleeve and blotting after 5 minutes.

Results are given below. Stain rating is on an 0 to 10 scale used by trained observers, unaware of which sample was treated with which agent(s). In this scale 0 is best and 10 is worst. The lightfastness was measured by AATCC 16E.

|  | Stain Rating | Lightfastness | |
|---|---|---|---|
|  |  | ΔE 120 AFU | Gray Scale* 120 AFU |
| 6a | 0.75 | 2.52 | 3.67 |
| 6b | 0.75 | 1.70 | 3.67 |
| 6c | 0.75 | 3.49 | 3.17 |

*Average

Improved lightfastness, i.e., less fading, is reflected by higher Gray Scale average and lower ΔE.

EXAMPLE 7

The effect of the process of this invention on the ozone fading of polyamides is illustrated as follows: samples of nylon 6 carpet, which had been treated with 2% OWF of a diphenyl ether-formaldehyde condensation product in the manner described in Example 1 except that the treatment bath temperatures were set at 110° F. (38° C.), 120° F. (49° C.), and 140° F. (60° C.) were treated for ozone fading by AATCC Method 129 (2 cycles) with the following results:

| Bath Temperature | 110° F. (38° C.) | 120° F. (49° C.) | 140° F. (60° C.) |
|---|---|---|---|
| Control*, Gray Scale Reading | 1–2 | 2 | 2 |
| Example 7, Gray Scale Reading | 3 | 2–3 | 3 |

*The control sample was treated only with DSR.

This invention relates to the preparation of novel chemical compounds and to novel methods of application to nylon (polyamide) materials (particularly polyamide fibers) which may or may not contain dyes wherein (a) the nylon materials and any incorporated dyes are afforded significant reduction in photodegradation and/or (b) the nylon materials are afforded significant improvement in resistance to many common stains, especially stains involving anionic species (such as FD & C Red 40, a common foodstuff dye) The novelty of the invention lies in (a) the chemical composition of certain of the additives which have not been previously reported and which provide significant and surprising photostability to polyamides and to dyes in polyamides at very low loadings relative to traditional photostabilizing additives, and (b) the method of application which provides for effective and durable incorporation into polyamides from aqueous solution under mild temperature conditions.

Traditional agents employed to enhance photostability of dyed polyamides include compounds of structures such as Tinuvin ® P Tinuvin 234

Cyasorb ® UV-54

Since these compounds are generally soluble only in organic solvents, the incorporation of such materials into nylon poses serious problems Surface application from organic solvents is a hazardous process and may result in a non-uniform coating of poor durability. Addition of these materials during extrusion may result in thermal degradation, ineffective distribution of material, and loss of material due to volatility under extruder conditions.

We have found that compounds of the general structure where M is a positive cation, such as an alkali metal or hydrogen, R is secondary alkyl, tertiary alkyl, tertiary aralkyl or hydrogen, for example,

STP may be effectively incorporated into nylon fiber from aqueous solution at relatively low pH (preferably pH <3) and at modest temperatures (0° C.–100° C., preferably 20–70° C.). Nylon fibers or dyed nylon fibers treated with this material (0.05–5 percent, preferably 0.1–1 percent by weight) either before or after dyeing show dramatically enhanced photostability relative to untreated materials. In addition, these fibers demonstrate increased resistance to staining by certain common stains, especially those containing anionic groups.

In addition, we have discovered that compounds of the general structures

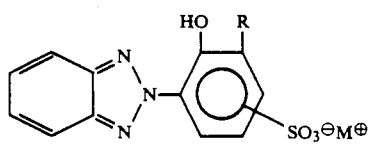

where R=secondary alkyl, tertiary alkyl or tertiary aralkyl, and particularly sulfonated T-234 (ST-234), which is a mixture of

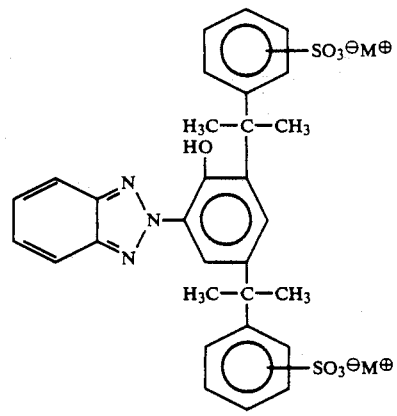

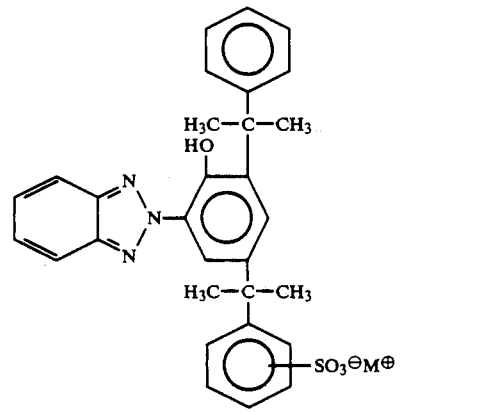

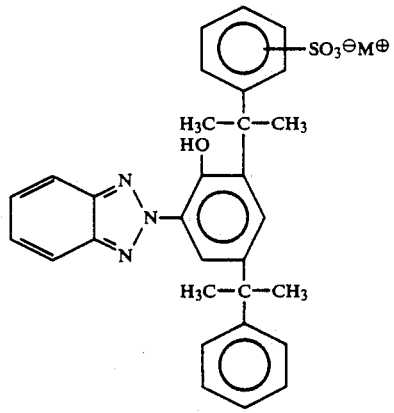

where M is a metal or hydrogen, and the SO₃⊖M⊕ group is para or ortho afford a surprising increase of stain resistance of nylon fiber and lightfastness of dye on nylon fiber.

EXAMPLE 8

Synthesis of Sulfonated Tinuvin P or STP.

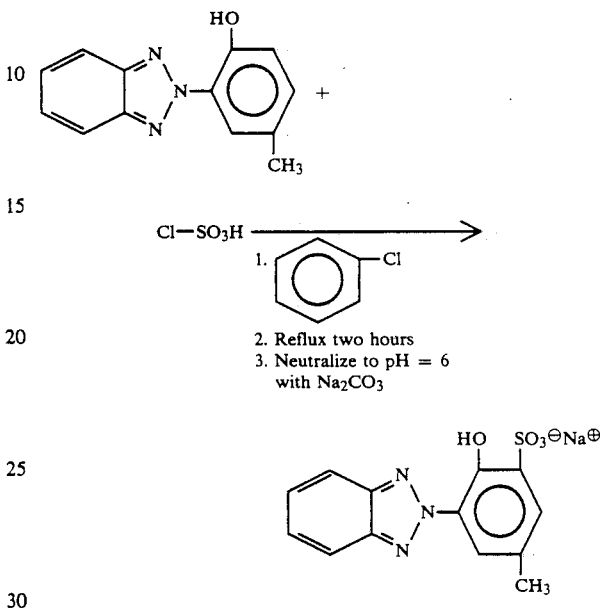

A solution of 53.5 grams (0.238 mole) of Tinuvin-P in 650 milliliters of chlorobenzene was added to a 1 liter round bottom one-neck flask equipped with a magnetic stirrer and heating mantle and set up for reflux under an atmosphere of nitrogen. Then 15.85 milliliters (0.238 mole) of reagent grade chlorosulfonic acid was slowly added to the stirred solution over a period of approximately twenty minutes. The resulting mixture was brought to reflux and maintained at reflux for 1½ hours. The solution was allowed to cool to room temperature under a slow stream of nitrogen. The contents of the flask were poured, with stirring, into a 2-liter beaker containing 300 grams of crushed ice.

The resulting emulsion was neutralized to pH=6.0 with 10 percent aqueous sodium carbonate solution. The solid product was filtered on a large Buchner funnel, using a medium speed filter paper. After several hours of air drying on the funnel, the resulting precipitate was washed with three 250-milliliter portions of toluene. The washed product was air-dried for ten hours. This nearly dry crude product was recrystallized from 4.5 liters of boiling water which had a pH=5 (adjusted with sulfuric acid). The precipitate was allowed to settle at room temperature for 12 hours, then cooled to approximately 5° C. in a refrigerator for three hours.

The resulting, finely divided, nearly colorless crystals were filtered on a coarse fritted glass funnel, and air dried for several hours. Actual yield of dry product was 51.6 grams, which is 71.2 percent of the theoretical yield.

EXAMPLE 9

Synthesis of St-234

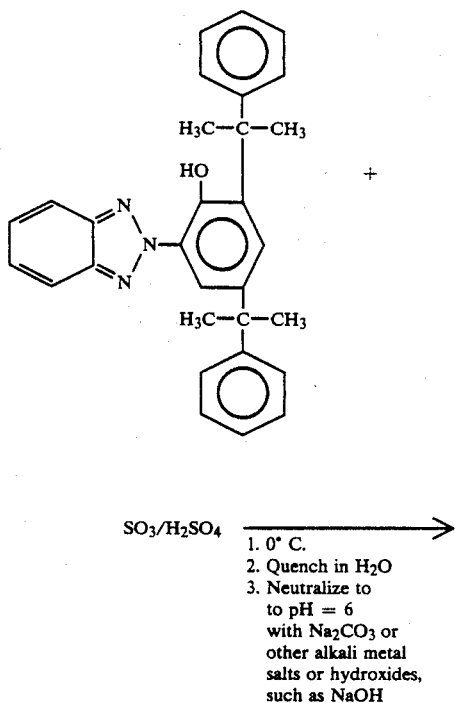

SO₃/H₂SO₄
1. 0° C.
2. Quench in H₂O
3. Neutralize to to pH = 6 with Na₂CO₃ or other alkali metal salts or hydroxides, such as NaOH

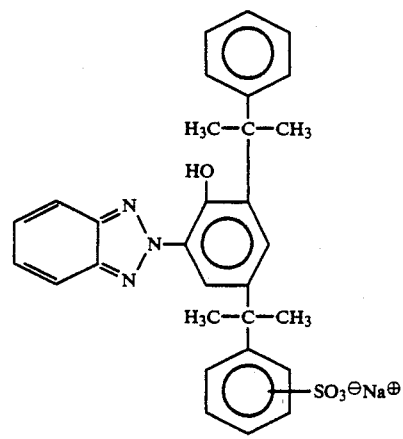

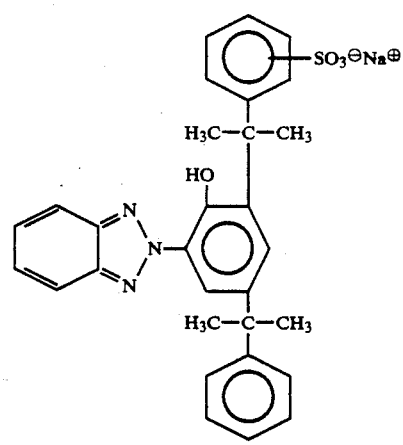

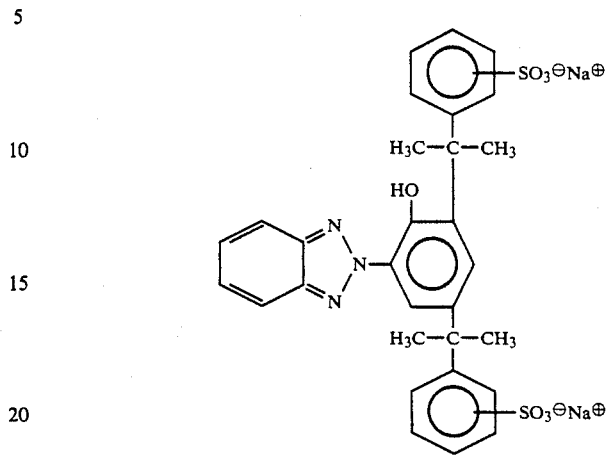

A solution of 5 percent fuming sulfuric acid was prepared by adding 2.3 milliliters of 20 percent fuming sulfuric acid to 6.8 milliliters of concentrated sulfuric acid (0.0105 mole of SO₃). Then 4.47 grams (0.0100 mole) of powdered Tinuvin-234 were slowly added to the vigorously stirred solution of fuming sulfuric acid which was maintained at a temperature below 25° C. Most of the Tinuvin-234 went into solution. The small residue of undissolved solid was allowed to stir at room temperature for about one hour until complete dissolution.

The yellow reaction mixture was quenched in 50 milliliters of ice water. The resultant mixture was neutralized to pH=7 with saturated aqueous sodium carbonate solution The resultant total volume was approximately 150 milliliters. This mixture was allowed to stand and settle for 12 hours. The precipitate was collected on a coarse glass fritted disc filter and washed three times with 20-milliliter portions of cold water. The precipitate was vacuum dried at 50° C. for 12 hours. The weight of dried product is nearly the theoretical amount, but contains a small percentage of co-precipitated sodium sulfate. This material was used to treat nylon for improved lightfastness without further purification.

EXAMPLE 10

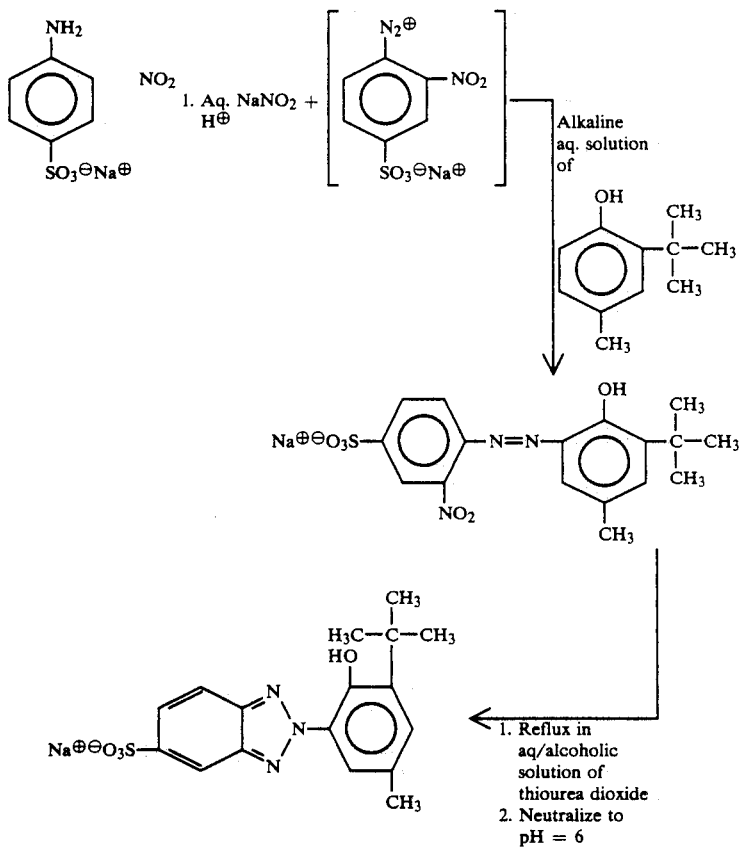

EXAMPLE 11

Photostability of UV Light Screens Dissolved in Polymer Film Matrices

| Light Screen Agent | Polymer | Destruction, %* |
|---|---|---|
| Tinuvin P | PMMA** | <9 |
| Tinuvin P | Nylon-6 | >65 |
| STP | PMMA | <9 |
| STP | Nylon-6 | >60 |
| Tinuvin 234 | PMMA | <7 |
| Tinuvin 234 | Nylon-6 | <5 |
| ST-234 | Nylon-6 | <5 |

*Twenty-one hours of irradiation in a Rayonet Photochemical Reactor equipped with RPR-3000 lamps at temperatures of 48–52° C. and ambient humidity. Amount of destruction determined by ultraviolet spectrophotometry.
**Polymethylmethacrylate.

This example demonstrates that hydroxybenzotriazoles lose photostability in a polyamide environment It also demonstrates that incorporation of bulky hydrophobic groups near the intramolecular hydrogen bond (especially in the ortho position relative to the hydroxyl) effectively provides for a high degree of photostability.

Typical Application Procedure

Beakers containing from 0.2 to 2.0 percent (OWF) of STP or ST-234 or other soluble UV screen with a 20:1 liquor ratio and adjusted to the proper pH were heated to 71° C. in a water bath (water bath had equilibrated at 71° C. before adding "dye" beakers). Samples of nylon knitted sleeve were added (usually 1 or 2 samples, each weighing approximately 5 grams) and stirred constantly for 30 minutes. The sleeves were removed after 30 minutes and rinsed with distilled water. After rinsing, the sleeves were padded with paper towels to remove excess water. The damp sleeves were then placed in an oven (~100° C.) for one hour. The dried samples were then allowed to equilibrate under ambient conditions, in the dark for at least 12 hours before irradiation testing.

Irradiation

Samples were suspended in a Rayonet RPR-100 Photochemical Reactor manufactured by The Southern New England Ultraviolet Company. For all of the irradiation testing reported, the reactor was fitted with 16 RPR-3000 lamps. The major output of these lamps is centered at 300 nanometers, with a significant 254 nanometers component and small amounts of radiation of longer wavelengths. No attempts were made to filter the output or restrict exposure to a specific bandwidth During all irradiations, the internal air circulation fan was operating. This resulted in operating temperatures of approximately 48° to 52° C. No attempt was made to control humidity.

The samples were suspended at the midpoint of the sources and rotated on a turntable to assure uniformity of irradiation. To further assure uniformity of exposure, the samples were rotated equally between direct front and back surface exposure. On longer term irradiations, the samples were cycled several times between ambient dark conditions and ambient irradiation conditions.

EXAMPLE 12

Protective Effects of Water-Soluble UV Light Screens on Undyed Nylon-6 Knitted Sleeves

| Additive* | pH | Exhaustion, %** | Color Before Irradiation | Color After Irradiation*** |
|---|---|---|---|---|
| Control | — | — | White | Yellow |
| STP | 2 | >95 | White | Light Yellow |
| ST-234 | 2 | >95 | White | Slightly Yellow |
| STP | 5 | 25 | Light Yellow | Yellow |
| ST-234 | 5 | 35 | White | Slightly Yellow |

*Applied at 71° C. from 20:1 liquor ratio bath. Nominally loading 0.1–2.0%.
**Percent bath exhaustion.
***Irradiation for 12 hours and for 40 hours in Rayonet Photochemical Reactor with RPR-3000 Lamps at 48–52° C. temperature and ambient humidity.

This example illustrates that uptake and color stability of nylon sleeves treated with sulfonated UV light screens is vastly superior for application at pH=2 relative to application at pH=5. Also, the superior performance of ST 234 to STP is demonstrated.

EXAMPLE 13

Protective Effects of Water-Soluble UV Light Screens on Dyed* Nylon-6 Knitted Sleeves

| Additive** | pH | Exhaustion, %*** | Color Before Irradiation | Color After Irradiation**** |
|---|---|---|---|---|
| Control | — | — | Normal | Severely Faded |
| STP | 2 | >95 | Slightly Off-Shade | Good Protection |
| ST-234 | 2 | >95 | Normal | Excellent Protection |
| STP | 5 | 25 | Off-Shade Yellow Coloration | Good Protection |
| ST-234 | 5 | 40 | Normal | Excellent Protection |

*Grey dyeing was with the following dyes at the following conditions.

| OWF, %(1) | |
|---|---|
| 0.0115 | Tectilon Orange 3G (100% strength) (C.I. Acid Orange 156) |
| 0.0121 | Tectilon Red 2B (100% strength) (C.I. Acid Red 361) |
| 0.0135 | Telon Blue BRL (200% strength) (C.I. Acid Blue 234) |

(1)On weight of fabric Dyeing Conditions: 1% Dowfax 2A1 2% monosodium phosphate pH 7 adj. w/trisodium phosphate Boil 30 minutes
**Applied at 71° C. from 20:1 liquor ratio, 0.1–2.0% (OWF) loading on non-DSR knitted sleeves. Similar results are obtained at room temperature.
***Percentage bath exhaustion, by spectrophotometric determination.
****After 12 hours irradiation in a Rayonet Photochemical Reactor with RPR-3000 lamps at temperatures of 48–52° C. and ambient humidity.

This example demonstrates that UV screens which are sulfonated and which possess a bulky hydrophobic group near the intra-molecular H-bond (such as ST-234) may be effectively applied to dyed nylon sleeves and that such materials provide superior light screening capability compared to similar compounds without such a hydrophobic group (i.e., STP).

BEST MODE

The compounds useful for this invention can be applied as an aftertreatment to dyed fibers, such as carpet face fibers, the preferred compounds are the ones labeled ST-234 above. The preferred method is described in Examples 6 and 15. In use a mixture of the mono- and disulfonated, both para and ortho isomers, are used. The compound may be applied in the aftertreatment either alone or in combination with other compounds, particularly those compounds which enhance stain resistance of the fibers, such as condensation product of formaldehyde with a diphenyl ether (hereinafter called DPE condensate), as described in Example 15. DPE condensate is described above in Examples 1 to 7.

The recommended aftertreatment conditions for ST-234 are 0.1 to 0.5 percent on weight of fabric (OWF) concentration in the aftertreatment bath, pH 2.1 (with citric acid), bath temperature 140° F. (60° C.), liquor to goods ratio 251, fabric time in bath 20 minutes.

EXAMPLE 14

The mixture of compounds labeled ST-234 above was used in an aftertreatment bath to treat nylon carpet fiber previously dyed to a silver-gray commercial carpet fiber color. Bath conditions were as set forth above except pH was 3.0, liquor to goods ratio was 30:1 and 0.47 percent (OWF) was applied. Lightfastness was improved over the control (no aftertreatment) to 1.45 $\Delta E$ from 4.12 $\Delta E$ for the control, or to an average Gray Scale rating of 3.5 at 120 SFU compared to control at 1.33 Gray Scale rating. Silver-gray dyeing was with the following dyes at the following conditions.

| OWF, %(1) | |
|---|---|
| 0.0104 | Tectilon Orange 3G (100% strength) (C.I. Acid Orange 156) |
| 0.0054 | Telon Red BRCL (250% strength) proprietary (Mobay) |
| 0.0126 | Telon Blue BRL (200% strength) (C.I. Acid Blue 324) |

(1)On weight of fabric Dyeing Conditions: 1% Dowfax 2Al 2% monosodium phosphate pH 7 adj. w/trisodium phosphate Boil 30 minutes

EXAMPLE 15

Staining Improvement

Using the recommended aftertreatment bath conditions given above, except temperature was 110° F. (43° C.), the mixture of compounds labeled ST-234 above, or the compound labeled STP above, either alone or with the stain resistance enhancer DPE condensate described above, were added to the aftertreatment bath for nylon carpet fiber in circular knitted sleeve form, predyed to the silver color described above. After treatment, stains were created with Cherry Kool-Aid ®, containing FD & C Red 40 food coloring, by forcing about 5 cubic centimeters of Cherry Kool-Aid ® into the fabric of the knitted sleeve of carpet fiber and blotting after five minutes. Results are given in the table below. Stain rating is on a 0 to 10 scale used by trained observers, unaware of which carpet fiber sample sleeve was treated with which compound. In the scale, low numbers mean good stain resistance and vice versa.

| Additive | OWF, % | Lightfastness $\Delta E$ 120 AFU | Gray Scale* 120 AFU | Stain Rating |
|---|---|---|---|---|
| None (Control) | 0 | 4.12 | 1.33 | 5 |
| DPE/STP | 2/0.5 | 2.52 | 3.67 | 0.75 |
| DPE/ST-234 | 2/0.5 | 1.70 | 3.67 | 0.75 |
| DPE | 2 | 3.49 | 3.17 | 0.75 |
| STP | 0.5 | 2.47 | 3.17 | 3.5 |
| ST-234 | 0.5 | 2.35 | 3.00 | 3.5 |

*Average, by AATCC 16E

Thus, it can be seen that STP and ST-234 compound improved the stain resistance considerably over the control, but that best stain resistance is dependent on use of DPE condensate, with or without STP or ST-234 compounds. However, the best overall combination of properties considering both lightfastness and stain resistance is the combination of DPE condensate with ST- 234 which had an ΔE rating of only 1.7, and average Gray Scale reading of 3.67. Low ΔE numbers and high Gray Scale numbers mean less fading.

The use of the compounds of the present invention are preferentially concentrated near the surface of, e.g., fibers of nylon to ensure optimum effective absorption of wave lengths of radiation which cause photodegradation of nylon and dyes in nylon. The anionic portion of these molecules ensures that they will be strongly attracted to nylon under the application conditions. However, the relatively hydrophobic remainder of the molecules will not readily migrate into the bulk of nylon. This unique balancing of effects results in optimal near-surface concentration of these light screens. This renders them remarkably effective both as UV light screens and as stain repelling agents.

We have discovered that compounds of the general structure photostability to polyamides relative to compounds VI and VII.

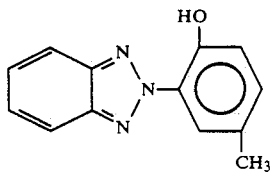

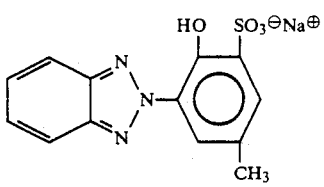

EXAMPLE 16

[structure of benzotriazole compound with tert-butyl and CH$_2$—CH$_2$—C(=O)—O—CH$_2$—CH$_2$)$_x$OH side chain] + ClSO$_3$H →

[structure of benzotriazole compound with tert-butyl and CH$_2$—CH$_2$—C(=O)—O—CH$_2$—CH$_2$)$_x$O—SO$_3^{\ominus}$Na$^{\oplus}$ side chain]

where x ≈ 6–7

1. [benzene–Cl, R.T.]

[structure V: benzotriazole with HO, R, and R'—O—SO$_3^{\ominus}$M$^{\oplus}$]

where R is a secondary alkyl, tertiary alkyl group, and M = hydrogen or metal, especially

[structure ST-1130: benzotriazole with tert-butyl and CH$_2$—CH$_2$—C(=O)—O—CH$_2$—CH$_2$)$_x$O—SO$_3^{\ominus}$Na$^{\oplus}$ side chain]

wherein the ionic sulfate group is located at the terminus of a heteroaliphatic chain of 6 to 30 atoms (preferably about 15 to 24 atoms) afford a surprising increase of 2. Neutralize to pH=6 with Na$_2$CO$_3$ or other base
3. Evaporate solvent to dryness The same procedure can also be used when x=8–9 or 12–13 or the entire range of 6–30.

EXAMPLE 17 (prospective example)

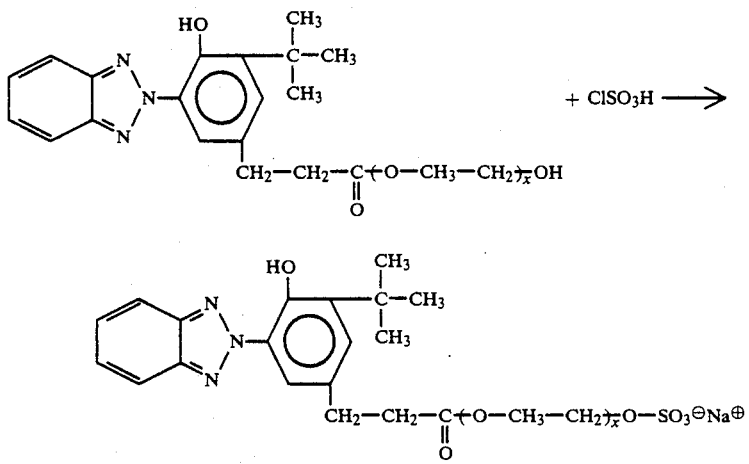

where x≈6-8

1. 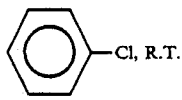

2. Neutralize to pH=6
3. Remove Solvent

The same procedure can also be used when x=16-22 or the entire range of 6-30.

EXAMPLE 18

Photostability of UV Light Screens Dissolved in Polymer Film Matrices.

| Light Screen Agent | Polymer | Destruction, *% |
|---|---|---|
| Tinuvin P | PMMA | <9 |
| Tinuvin P | Nylon-6 | >65 |
| STP | PMMA | <9 |
| STP | Nylon-6 | >60 |
| Tinuvin 1130 | PMMA | >13 |
| Tinuvin 1130 | Nyon-6 | >5 |
| ST-1130 | PMMA | >5 |
| ST-1130 | Nylon-6 | >5 |

*Twenty-one hours of irradiation in a Rayonet Photochemical Reactor equipped with RPR-3000 lamps at temperatures of 4-52° C. and ambient humidity. Amount of destruction determined by ultraviolet spectrophotometry.

This example demonstrates that hydroxybenzotriazoles lose photostability in a polyamide environment. It also demonstrates that incorporation of bulky hydrophobic groups near the intramolecular hydrogen bond (especially in the ortho position relative to the hydroxyl group) effectively provides for a high degree of photostability.

EXAMPLE 19

Protective Effects of Water-Soluble UV Light Screens on Undyed Nylon-6 Knitted Sleeves.

| Additive[1] | pH | Uptake, %[2] | Color Before Irradiation | Color After Irradiation[3] |
|---|---|---|---|---|
| Control | — | — | White | Yellow |
| STP | 2 | >95 | White | Light Yellow |
| ST-1130 | 2 | >95 | White | Slightly Yellow |
| STP | 5 | 25 | Light Yellow | Yellow |

-continued

| Additive[1] | pH | Uptake, %[2] | Color Before Irradiation | Color After Irradiation[3] |
|---|---|---|---|---|
| ST-1130 | 5 | 55 | White | Slightly Yellow |

[1]Applied at 71° C. from 20:1 liquor ratio bath. Nominal loading 0.1-2.0%.
[2]Percent bath exhaustion.
[3]Irradiation for 12 hours in a Rayonet Photochemical Reactor with RPR-3000 Lamps at 4-52° C. temperature and ambient humidity.

This example illustrates that uptake and color of nylon sleeves treated with anionic, sulfated UV light screens is vastly superior for application at pH=2 relative to application at pH=5. Also, the superior performance of ST 1130 relative to STP is demonstrated.

EXAMPLE 20

Protective Effects of Water-Soluble UV Light Screens on Dyed[1] Nylon-6 Knitted Sleeves.

| Additive[2] | pH | Exhaustion, %[2] | Color Before Irradiation | Color After Irradiation[4] |
|---|---|---|---|---|
| Control | — | | Normal | Severely Faded |
| STP | 2 | >95 | Slightly Off-shade | Good Protection |
| ST-1130 | 2 | >95 | Normal | Excellent Protection |
| STP | 5 | 25 | Off-shade Yellow Coloration | Good Protection |
| ST-1130 | 5 | 55 | Normal | Excellent Protection |

[1]Dyed with 0.1% (OWF) argent grey
[2]Applied at 71° C. from 20:1 liquor ratio, 0.1-2.0% (OWF) loading on non-DSR knitted sleeves.
[3]Percentage bath exhaustion, by spectrophotometric determination.
[4]After 12 hours irradiation in a Rayonet Photochemical Reactor with RPR-3000 lamps at temperatures of 48-52° C. and ambient humidity.

This example demonstrates that UV screens which are rendered anionic by sulfation and which possess a bulky hydrophobic group near the intramolecular H-bond (such as ST-1130) may be effectively applied to dyed nylon sleeves and that such materials provide superior light screening capability compared to similar compounds without such a hydrophobic group (i.e., STP).

What is claimed:

1. A sulfonated 2-(2'-hydroxyaryl)-2H-benzotriazole selected from the group consisting of the following chemical structure

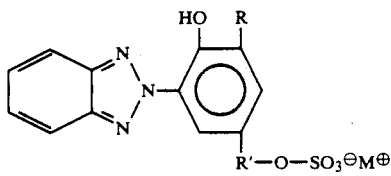

wherein R is a secondary alkyl, tertiary alkyl group, R' is a polyether chain of 5 to 69 carbon atoms, and M is hydrogen, ammonium or a metal ion which does not result in a highly colored benzotriazole.

2. The benzotriazole of claim 1 wherein the structure is

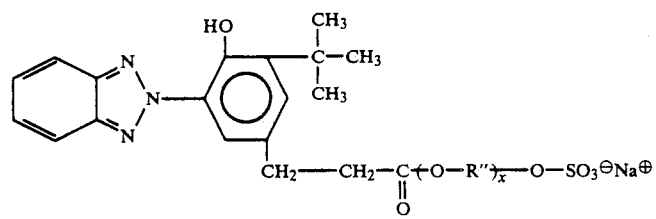

wherein x is 1 to about 22 and R'' is —CH$_2$CH$_2$— or

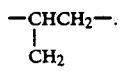

3. The benzotriazole of claim 1 wherein the metal ion is selected from the group consisting of aluminum, magnesium, lithium, sodium, potassium and zinc.

4. A water soluble sulfonated 2-(2'-hydroxyaryl)-2H-benzotriazole selected from the group consisting of the following chemical structure

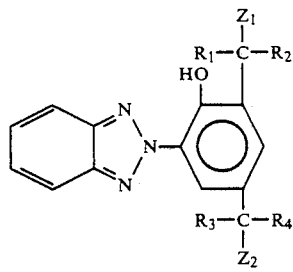

ST-1130 wherein R$_1$, R$_2$, R$_3$ and R$_4$ are independently the same or different alkyl groups and Z$_1$ and Z$_2$ are alkyl or sulfonated aryl group, provided at least Z$_1$ or Z$_2$ is sulfonated aryl group, and wherein said alkyl contains from one to about thirty carbon atoms, such aryl is carbocyclic of up to four cycles and said sulfonated aryl is such that the resulting said benzotriazole is water soluble.

5. The benzotriazole of claim 4 wherein the aryl is selected from the group consisting of phenyl, naphthyl, anthryl and phenanthryl.

* * * * *

UNITED STATES PATENT AND TRADEMARK OFFICE
CERTIFICATE OF CORRECTION

PATENT NO. : 4,990,623

DATED : February 5, 1991

INVENTOR(S) : Paul W. Harris

It is certified that error appears in the above-identified patent and that said Letters Patent is hereby corrected as shown below:

On the title page, item [76], delete "Morris B. Berenbaum, 59 Crest Dr., Summit, N.J. 07901; John H. Bonfield, 183 Lyons Dr., Basking Ridge, N.J. 07920; Charles J. Cole, 11560 Teterling Rd.;" and "Thomas P. J. Izod, 112 Victoria Dr., Basking Ridge, N.J. 07920; Harry E. Ulmer, Rte. 2, Box 3, Cameron, S.C. 29030;".

Item (19) should read " Harris".

Signed and Sealed this

Fourth Day of June, 1991

*Attest:*

HARRY F. MANBECK, JR.

*Attesting Officer*    *Commissioner of Patents and Trademarks*